US008475385B2

(12) United States Patent
Watson

(10) Patent No.: US 8,475,385 B2
(45) Date of Patent: Jul. 2, 2013

(54) METHOD AND APPARATUS FOR PHYSIOLOGICAL MONITORING

(75) Inventor: Marcus Watson, Westlake (AU)

(73) Assignee: The University of Queensland, St Lucia, Queensland (AU)

( * ) Notice: Subject to any disclaimer, the term of this patent is extended or adjusted under 35 U.S.C. 154(b) by 1378 days.

(21) Appl. No.: 11/665,647

(22) PCT Filed: Oct. 19, 2005

(86) PCT No.: PCT/AU2005/001622
§ 371 (c)(1), (2), (4) Date: Apr. 18, 2007

(87) PCT Pub. No.: WO2006/079148
PCT Pub. Date: Aug. 3, 2006

(65) Prior Publication Data

US 2008/0114216 A1 May 15, 2008

(30) Foreign Application Priority Data

Oct. 19, 2004 (AU) ................................ 2004906016

(51) Int. Cl.
*A61B 5/02* (2006.01)

(52) U.S. Cl.
USPC ............................................ 600/485; 84/600

(58) Field of Classification Search
USPC ................. 600/322, 323, 326, 485, 500, 502, 600/508, 530, 538, 561; 84/600–609
See application file for complete search history.

(56) References Cited

U.S. PATENT DOCUMENTS 2,821,188 A 1/1958 Pigeon
3,658,060 A 4/1972 Eklof
3,732,868 A * 5/1973 Willems et al. ............... 600/514
3,830,227 A * 8/1974 Green ........................... 600/514
4,510,943 A 4/1985 Miyamae
4,576,178 A * 3/1986 Johnson ........................ 600/483
5,095,896 A * 3/1992 Omoigui .................. 128/200.26

(Continued)

FOREIGN PATENT DOCUMENTS

JP 05-040049 2/1993
JP 05 317269 12/1993

(Continued)

OTHER PUBLICATIONS

McGookin and Brewster, “An Investigation into the Identification of Concurrently Presented Earcons,” Jul. 2003. Proc. of the 2003 Int'l Conf. on Auditory Display, pp. ICAD03-1 to ICAD03-4.*

(Continued)

*Primary Examiner* — Navin Natnithithadha
*Assistant Examiner* — Eric Messersmith
(74) *Attorney, Agent, or Firm* — Nixon & Vanderhye P.C.

(57) ABSTRACT

Blood pressure measurements are represented aurally. An audio synthesizer (15) receives a signal representative of blood pressure information, and synthesizes an audio output from the signal. Both the duration and pitch of the synthesized audio output are dependent on the value of the blood pressure information, according to a linear scale or a non-linear scale such as stepped scale. The blood pressure information includes at least one of arterial or pulmonary arterial systolic, diastolic and mean blood pressure measurements, and the audio output includes an earcon comprising a tone or sequence of tones, the tone(s) being representative of a respective type of blood pressure measurement. The earcon may also include one or more static or dynamic beacons.

12 Claims, 5 Drawing Sheets

10
11
12
13
14
15
16

U.S. PATENT DOCUMENTS

| | | | | |
|---|---|---|---|---|
| 5,285,521 | A * | 2/1994 | Holt et al. | 704/270 |
| 5,360,005 | A * | 11/1994 | Wilk | 600/437 |
| 5,371,854 | A * | 12/1994 | Kramer | 704/270 |
| 5,730,140 | A * | 3/1998 | Fitch | 600/514 |
| 5,836,302 | A * | 11/1998 | Homuth et al. | 128/205.23 |
| 6,449,501 | B1 * | 9/2002 | Reuss | 600/323 |
| 6,704,413 | B1 * | 3/2004 | Weeks et al. | 379/374.01 |
| 6,947,780 | B2 | 9/2005 | Scharf | |
| 7,112,175 | B2 * | 9/2006 | Gopinathan et al. | 600/508 |
| 7,138,575 | B2 * | 11/2006 | Childs et al. | 84/615 |
| 2004/0055447 | A1 * | 3/2004 | Childs et al. | 84/615 |
| 2005/0209515 | A1 * | 9/2005 | Hockersmith et al. | 600/316 |

FOREIGN PATENT DOCUMENTS

| | | |
|---|---|---|
| JP | 07-227382 | 8/1995 |
| JP | 2001-245856 | 9/2001 |
| WO | 03/017838 | 3/2003 |

OTHER PUBLICATIONS

International Search Report for PCT/AU2005/001622 mailed Jan. 16, 2006.

Chang et al., *The Development of a Signal Processing System for Converting Arterial Blood Pressure to Sound*, IEEE EMBS Asian-Pacific Conference, publication date Oct. 20-22, 2003, pp. 252-253.

Supplementary European Search Report—issued in corresponding European Patent Application No. EP05856175 on Jan. 28, 2010 and Examination Report.

Haas, E.C., et al, *Computing & Control Engineering Journal*, Aug. 1996, pp. 193-198, "Designing urgency into auditory warnings using pitch, speed and loudness," XP-002565614.

Loeb, Robert G., et al, *Anesth Analg* 2002, 94: 362-368, "A Laboratory Evaluation of an Auditory Display Designed to Enhance Intraoperative Monitoring," XP-002565615.

Jungk, A. et al, *Journal of Clinical Monitoring and Computing*, (2000) 16: 243-258, "Evaluation of two new ecological interface approaches for the anesthesia workplace."

Zhang, Y. et al, *Cognition, Technology & Work*, (2002) 4: 82-90, "Effects of integrated graphical displays on situation awareness in anaesthesiology."

Watson, M. et al, *Interacting with Computers*, (2004) 16: 271-293, "Tailoring reveals information requirements: the case of anaesthesia alarms."

Seagull, F.J. et al, *Human Factors*, Spring 2001, 43: 66-78, "Anesthesia Alarms in Context: An Observational Study."

Watson, Dr. Marcus, et al, (in press) Earcon for Intermittent Information in Monitoring Environments. To appear in the Proceedings of the Australian/New Zealand conference on Computer-Human Interaction (OzCHI04), The University of Wollongong, Australia. Nov. 22-24, 2004.

Anderson, J. et al, Proceedings of the Human Factors and Ergonomics Society 48$^{th}$ Annual Meeting—2004; p. 1818-1822; "Designing Sonification for Effective Attentional Control in Complex Work Domains."

Sharp, T.D, Helmicki, A.J., "Application of the Ecological Interface Design Approach to Neonatal Intensive Care", Human Factors and Ergonomics Society, 42nd Annual Meeting, Oct. 1998.

Xiao, Y., Mackenzie, C.F., Seagull, F.J., & Jaberi, M. (2000). Managing the monitors: An analysis of alarm silencing activities during an anesthetic procedure. Proceedings of the Joint Meeting of The Human Factors and Ergonomics Society and the International Ergonomics Association (IEA 2000/HFES 2000). (pp. 250-253). Santa Monica, CA: HFES.

Bryan, W.L., & Harter, N. (1897). Studies in the physiology and psychology of telegraphic language. Psychological Review, 4, 27-53.

* cited by examiner

METHOD AND APPARATUS FOR PHYSIOLOGICAL MONITORING

This application is the US national phase of international application PCT/AU2005/001622 filed 19 Oct. 2005 which designated the U.S. and claims benefit of AU 2004906016, filed 19 Oct. 2004, the entire content of each of which is hereby incorporated by reference.

FIELD OF THE INVENTION

This invention relates to a method and apparatus for monitoring blood pressure. In particular, but not exclusively, it relates to an improved method and apparatus for auditory display of blood pressure readings during anaesthesia and intensive care to enable blood pressure to be monitored aurally.

BACKGROUND OF THE INVENTION

Mere reference to background art herein should not be construed as an admission that such art constitutes common general knowledge or admissible prior art in relation to this application.

Blood pressure is a fundamental cardiovascular parameter that represents the force that drives perfusion of the body and in part reflects the workload of the heart [1]. There are difficulties in obtaining a meaningful reading of blood pressures; first, different techniques produce significantly different readings and second, blood pressure can change significantly due to environmental or emotional changes. To better utilise blood pressure information to interpret patient events, clinicians require blood pressure trend information preferably combined with other relevant physiological measures of the patient such as capnography. At present, blood pressure trend information is either gathered by invasive measures that provide continuous information or through non-invasive measurements of blood pressure (NIBP) that provide intermittent information.

Interpreting the different measurements of blood pressure in relation to other physiological parameters can be difficult due to the low rate of sampling of the visually displayed information by the clinicians. This is especially problematic when using automatic NIBP, as the time elapsed since the last measurement might be unknown, and it is not immediately apparent whether a loss of information is due to failure within the machine or the patient [1].

Blood pressure is normally represented using numerical and graphical visual displays, and abnormal states may be indicated with auditory alarms. There are a range of proposed displays that integrate data, including blood pressure, graphically in a way that shows higher order properties of the anesthetized patient's state [2]-[4]. These displays are dependent upon the clinician's ability to attend to the visual display, which is not always possible [5]. Further, these displays do not convey blood pressure in the auditory modality nor do they distinguish between intermittent and continuous measurements of physiological parameters. There is strong evidence showing that auditory alarms are not particularly effective at directing clinicians' attention to visual displays [5]-[7]; therefore, even if the proposed visual displays are of benefit in providing integrated data, it is likely that people in care-providing environment are likely to miss some important information on the visual displays.

Other approaches have attempted to sonify blood pressure as part of a multi-parameter continuous auditory display [8]. These sonifications have at least four problems. First, the blood pressure information may not be continuously measured and therefore the inclusion of such a parameter may be misleading as the blood pressure may have changed since the last value was measured. This is potentially very dangerous since clinicians' diagnoses may be made on the basis of incorrect information [5]. Second, the blood pressure information has to be separated out from the sonification by focusing on one or more sound dimensions. Third, no historical information is included in the sonification. Fourth, the sonification has not been designed to support integration across the visual and auditory modalities.

U.S. Pat. No. 6,947,780 discloses method and apparatus for sonification of physiological data, and in particular blood oximeter readings. An audio signal is generated at each pulse, dependent upon the measured oximeter reading. If the measurement corresponds to one of a plurality of pre-determined transition points in a range, a tone of a respective frequency is generated. For readings which fall between a pair of the transition points, a dual tone signal is generated. The dual tone signal comprises two frequencies, each of which has its amplitude modified by a respective factor which depends upon the proximity of the reading to the pair of transition points. Although no evaluation data is presented for this system of sonification, it seems likely that clinicians would find it difficult to distinguish between tones of closely spaced frequencies and between different amplitudes, particularly at typical pulse rates.

International patent application WO 03/017838 discloses sonification of respiratory behaviour. That method uses tones of different pitch to represent different levels of measured respiratory parameters, e.g. respiratory flow and carbon dioxide concentrations. A clinician or other user must distinguish aurally between parameter values on the basis of pitch alone.

It is an aim of the present invention to provide an improved method and apparatus for monitoring blood pressure, which overcome or alleviate one or more of the limitations and disadvantages of prior art blood pressure monitoring systems, particularly during anaesthesia and intensive care, or which at least provide the public with a useful choice.

STATEMENT OF THE INVENTION

In one broad form, the invention provides a method of representing or displaying blood pressure of a subject aurally, comprising the steps of receiving a signal representative of blood pressure information, and synthesising an audio output from the signal, wherein the duration and pitch of the synthesised audio output are dependent on the blood pressure information.

In another broad form, the invention provides an apparatus for representing or displaying blood pressure of a subject aurally, comprising an audio synthesizer adapted to receive a signal representative of blood pressure information and to synthesize an audio output from the signal, wherein the duration and pitch of synthesized audio output are dependent on the value of the blood pressure information.

The blood pressure information typically includes at least one of arterial or pulmonary arterial systolic, diastolic and mean blood pressure measurements, obtained by invasive or non-invasive means. This information, if not already in digital form, is suitably converted to digital form by a signal processor connected to the input of the audio synthesizer.

The audio output preferably includes an earcon comprising a tone or sequence of tones, the tone(s) being representative of a respective type of blood pressure measurement. For example, systolic and diastolic blood pressure readings may be sonified as two separate tones in the earcon.

In use, changes in the systolic, diastolic and/or mean blood pressure of the subject are represented and monitored aurally as changes in the synthesized audio output, typically heard through a loudspeaker, headphone or earpiece.

Auditory assessment of the blood pressure information is facilitated by using both the duration and the pitch of the synthesised audio output as aural indicators of the blood pressure information. The term 'pitch' is intended to mean the frequency, or primary frequency, of the relevant tone in the audio output.

Both current and historical blood pressure readings may be included in an earcon, to facilitate the detection of changes in blood pressure. For example, the earcon may comprise a first note representing the previous blood pressure reading, followed by a second note representing the current blood pressure reading.

Preferably, the earcon includes a beacon, i.e. a note representing a predetermined value of the measured parameter. For example, the earcon may comprise a first note (i.e. the beacon) representing the average, normal or desired blood pressure, followed by a second note representing the current blood pressure reading. This facilitates a ready aural comparison of current blood pressure with an average or desired reading.

Any suitable combination of single or double beacons, and current and/or historical readings of systolic, diastolic and/or mean blood pressure, may be included in the earcons. An auditory prompt may also be given prior to each earcon to warn of the imminent auditory signal.

Where the earcon includes a plurality of tones, they may be distinguished by adding harmonics to the primary frequencies of the tones. This provides timbre to the sound, although the fundamental or primary frequency remains the same.

A linear or non-linear scale may be used to calculate the duration and pitch of synthesized audio output from the blood pressure information signal. In a preferred embodiment, a stepped scale is used. The value of the signal is mapped to a nine step scale, and represented by a corresponding one of a series of nine notes of progressively increasing pitch. Similarly, the duration of the synthesized audio output is one of a possible three discrete periods of progressively increasing length, the particular duration being dependent upon the mapping of the signal to a nine part scale. Thus, a low blood pressure value would be represented by a short low note, while a high blood pressure value would be represented by a long high-pitched note. However, other suitable forms of scaling may be used.

Preferably, the apparatus also includes a user interface which typically has a volume control to adjust the overall volume of the auditory output, a selection control to select the type of blood pressure represented, a selection control to select the length of signal interval, a selection control to select the type of beacon, and/or a selection control to select the historical information.

The user interface means may be an electronic or electromechanical control means.

In order that the invention may be better understood and put into practice, a preferred embodiment thereof will now be described, by way of example only, with reference to the accompanying drawings.

DETAILED DESCRIPTION OF AN EMBODIMENT OF THE INVENTION

Figure 1:
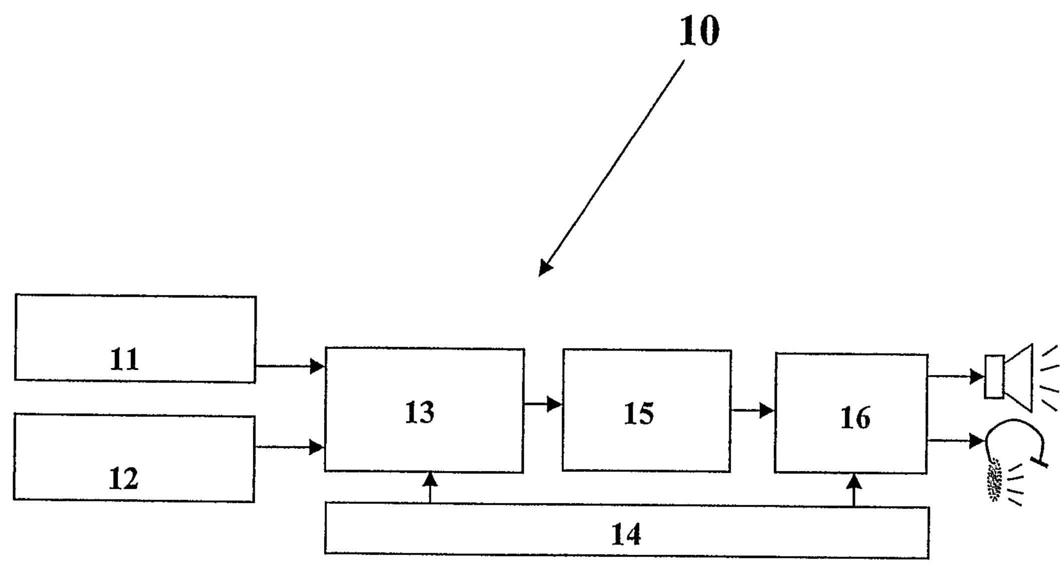
FIG. 1 is a block diagram of one embodiment of the apparatus of this invention.

A block diagram of a sonification apparatus 10 according to one embodiment of the invention is shown in FIG. 1. The sonification apparatus is primarily a software driven device adapted to be used with an existing anaesthetic system and to use the existing anaesthetic system's visual monitor and speaker. It can also work with portable monitoring devices capable of measuring blood pressure.

The apparatus includes an input 11 which receives readings of systolic, diastolic and mean arterial or pulmonary arterial blood pressure levels, typically in digital form. (If the readings are in analogue form, they are converted to digital). Most anaesthetic monitoring systems are equipped with one or more measuring devices to obtain such readings, and they need not be described in detail in this application. These devices may also be found on non-anaesthetic monitors. The apparatus 10 also includes a memory 12 for storing previous readings.

The apparatus 10 includes a signal processing and mapping unit 13 which processes the systolic and diastolic digital information received from 10. The unit 13 receives digital information about the type of measurement, the user's beacon selection, historical information, the parameter selection and the blood pressure measurement selected, through a user interface 14. If historical information is requested, this will be recalled from memory 12. If the type of measurement selected is continuous, then the signal processor 13 will also receive information about the rate of update for the visual and auditory display through the user interface 14.

The signal processing and mapping unit 13 also maps the blood pressure readings to a scale, as described in more detail below, for expression in auditory form as a component note or tone in an earcon.

The output of the signal processing and mapping unit 13 is sent to a sound synthesizer 15 which generates the musical or pitch scale and sound duration according to the earcon sound dimensional mapping. That is, the pitch (frequency) and duration of the audio output tone are dependent on the measured value of the blood pressure reading. The earcon may comprise four aural components or tones, representing the type of blood pressure being measured, a beacon, the current measure of blood pressure, and a historical measure of blood pressure, respectively.

The synthesized earcons are then sent to an audio output device 16 which may be a speaker or an earpiece.

Figure 2A:
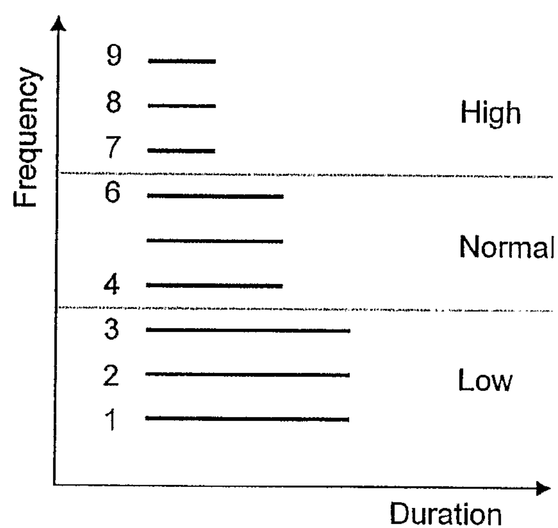
FIGS. 2A and 2B illustrate example mappings of blood pressure parameters into the sound dimensions of the earcon.
Figure 2B:
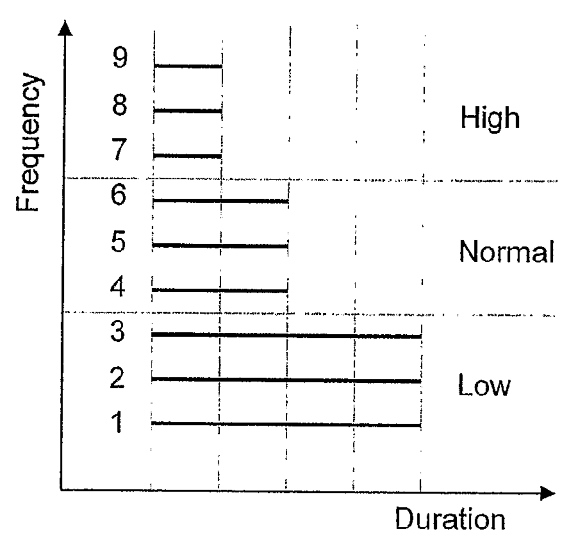

In a preferred embodiment, the mapping of the blood pressure measurements uses, but is not limited to, a nine-point scale. The auditory scale indicates high, normal and low levels, and sub-levels within each range, as shown in FIGS. 2A and 2B.

Each point on the scale is indicated by a unique combination of duration and pitch. The duration of each point is mapped but not limited to the overarching range, such that all points in the low range of the scale will have the same duration, all points in the normal range of the scale will have the same duration and all points in the high range of the scale will have the same duration. The difference in duration length between low, normal and high will preferably be, but is not limited to, a ratio of either 1:2:3 (as shown in FIG. 2A) or 1:2:4 (as shown in FIG. 2B). Each point on the scale will also have a mapping to a pitch or musical scale that will significantly differentiate each point on the scale.

In the case of a non-invasive reading, the blood pressure results are sent to the synthesizer 13 immediately the measurement is completed. In the case of an invasive measurement where arterial and/or pulmonary arterial measurements are updated with every heartbeat, the earcons will be updated according to the type of measurement selected. If a time interval basis is selected, then the results will be updated every time that time interval has lapsed. If the type of measurement selected is a change-based one, then an earcon will be output whenever a blood pressure measurement, (systolic, diastolic or mean blood pressure) changes from one region of the mapping to another.

The user interface 14 allows the user to: select the type of measurement selected (intermittent or continuous); the user's beacon selection (none, static or dynamic); historical information (none or previous measurement stored in memory); the parameter selection (arterial or pulmonary arterial); the blood pressure measurement (systolic, diastolic or mean blood pressure); and the rate of update for the visual and auditory display in the continuous setting (or upon a change in blood pressure and/or time elapsed).

Examples of typical types of earcon selections and settings are given in Table 1 which lists possible user selected components of the blood pressure earcons. These can be presented in any order including repeated presentations in the earcons. Each condition is able to play an associated wave file determined by the measurement it represents.

Figure 3A:
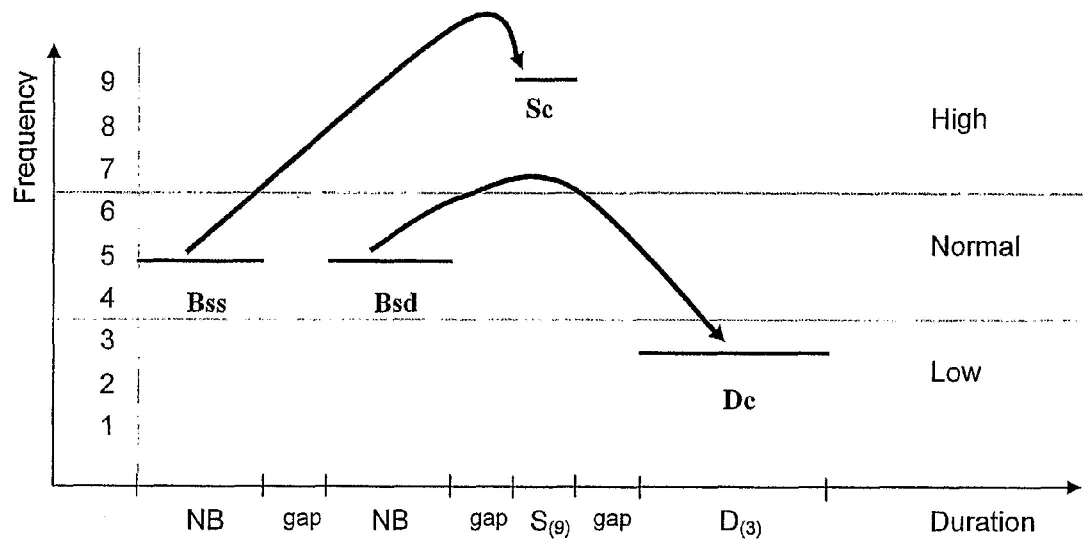
FIGS. 3A and 3B illustrate the use of static and dynamic beacons.
Figure 3B:
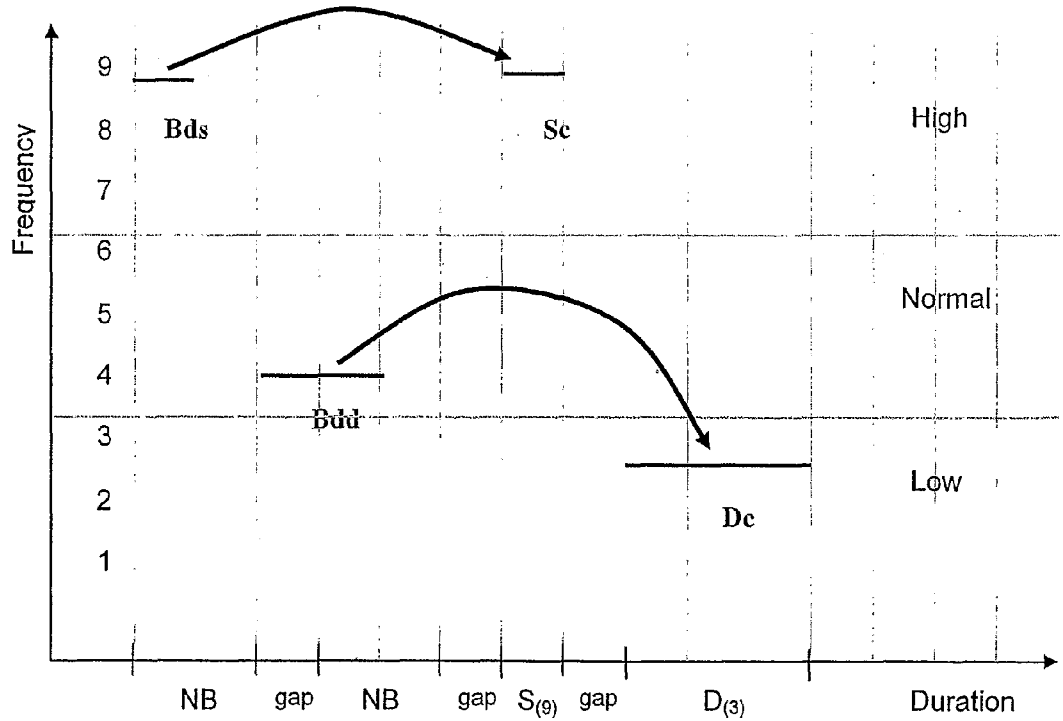

The beacons may be static or dynamic. Comparison of a static beacon with a dynamic beacon is shown in FIGS. 3A and 3B. In a static beacon (FIG. 3A), the listener compares the 'normal' level for rhythm, pitch and duration against the sound heard in the earcon. As shown by the arrows, the first part Bss of the static beacon is compared against the current systolic value Sc; the second part Bsd of the static beacon is compared against the current diastolic value Dc. The rhythm assists with the assessment of duration. The difference between relative duration and pitch also helps assess value.

In a dynamic beacon (FIG. 3B), the listener compares either a user defined beacon or one captured by the system from a previous measurement. Again, as shown by the arrows, the first part Bds of the beacon is compared against the systolic value; and the second part Bdd of the beacon is compared against the diastolic value. This is more effective at detecting change from an expected state rather than judging absolute value A user can also adjust the blood pressures scales which are indicated by a changed background on the visual display. The user can also adjust the overall volume of the earcons.

The method and apparatus described above have several advantages over known sonification systems, including:

- Both the pitch (frequency) and duration of the earcon tones represent the measured readings, thereby facilitating aural recognition.
- Three dimensions of sound, namely tempo, duration and pitch, are used to indicate the range for beacons, systolic, diastolic and mean arterial blood pressure in a short auditory motif.
- The blood pressure earcons can work alongside existing commercial pulse oximetry systems rather than being part of a system for sonifying a broader range of physiological variables including cardiovascular variables.
- The beacons and systolic, diastolic or mean blood pressure values are distinguishable by the order they occur and the harmonics associated with mode selected.
- The earcons are distinguishable between intermittent and continuous measurements of blood pressure by both the rate and pattern of the display.
- The arterial and pulmonary arterial earcons can be distinguished by the use of different harmonics to the primary frequencies.
- Similarly the difference between the static beacon and the dynamic beacon can be indicated by adding reverberation to the sound stream.
- The rhythm produced by the gaps between sounds in the earcon can assist with the categorisation of the pitch and duration.
- During non-invasive blood pressure monitoring of a patient, the earcon will sound when a blood pressure measurement is taken.
- During invasive blood pressure monitoring, the earcons will sound according to the selection made by the clinician; combining one or both of time elapsed since the last earcon and any occurrence of a blood pressure change.

Empirical Evaluation of the Earcons and Beacons

Two studies were conducted to examine the following performance aspects:

H1 The accuracy achieved when participants rely on the auditory display alone should be comparable to people's ability to monitor physiological parameters with other auditory displays or visual displays.

H2 The earcons should be perceivable against background sounds that could be found in the monitoring environment.

H3 The presence of a beacon should assist participants with the interpretation of earcons for systolic and diastolic blood pressure.

H4 The benefit of historical systolic and diastolic information in the earcon for recalling previous measurements and identifying changes between the previous and current measurements.

H5 Beacons assist participants with their judgments of the earcon due to the recognition of the rhythm, pitch and duration difference in the sound rather than alerting the participants to shift attention.

EXAMPLE 1

Comparison of Earcon Constructs for Intermittent Information

The first study addressed issues related to H1 to H14. From a comparison between three of the possible earcons, it was sought to establish that historical information and the static beacon would assist participants' awareness of the simulated patient's blood pressure.

The first experiment compared three versions of the earcons under a dual task condition. Participants monitored a simulated patient while conducting a basic but cognitively demanding arithmetic task [9].

A within-subject experiment was conducted with three independent variables. The first variable was earcon type. The first earcon provided information about the current systolic and diastolic blood pressure measurements (referred to as C); a second earcon contained the beacon followed by the current systolic and diastolic blood pressure measurements (referred to as BC); a third earcon contained the beacon followed by the previous historical blood pressure measurements, then the current systolic and diastolic blood pressure measurements (referred to as BPC). The beacons used in these trials consisted of a static beacon for systolic and diastolic blood pressure measurements.

The second variable was blood pressure history with levels prior and present.

The third variable was blood pressure measure, with levels systolic and diastolic.

There were two dependent variables, earcon plotting accuracy and the accuracy of the responses to the arithmetic task.

Twenty-four people without medical qualifications participated in a within-subject repeated measures design to assess the earcons in a dual task paradigm [9]. Participants monitored blood pressure change while completing a simple but also time consuming arithmetic task. (The arithmetic task required the participants to assess whether a simple sum was true or false, e.g. 7+1=8.) A dual task paradigm was used to simulate similar repetitive tasks performed by anaesthetists that might distract from patient monitoring. The dual task was also used to assess the attentional issues of switching between unrelated tasks. The arithmetic task required the participants to process information and recall response from memory that had the potential to interfere with their memory of the previous blood pressure measurement. It was also possible that there could be an increase in earcon recognition errors if the participants had to refocus their attention from the visual arithmetic task to the auditory blood pressure monitoring task.

Participants received 45 minutes of training through a POWERPOINT™ presentation built to familiarise them with the earcons and the arithmetic task. The earcon stimuli were composed of nine 10-minute soundtracks in each condition (C, BC and BPC). The soundtracks were composed of a backing track of respiratory and cardiac sonifications, with the earcons placed at 2 minute intervals. From related work it was known that participants could attend to more than one sound stream [5],[10]; therefore, the presence of blood pressure beacons should not inhibit the monitoring of other physiological parameters or be inhibited by the presence of other auditory information.

The first earcon occurred less than one minute into each soundtrack. Participants listened to three soundtracks per condition and the condition order was counter-balanced across participants. Participants recorded their estimates for the previous and the current values of systolic and diastolic blood pressure on a nine-point scale. Responses were recorded on a new results sheet every time participants heard the earcons, to prevent participants referring to their previous answers. Participants also answered a series of questions throughout the experiment on their subjective experiences of the earcons.

Participants' results for the arithmetic task, earcon performance and questionnaire responses were analysed using a series of ANOVAs and tests of contrasts. There were no significant differences of earcon type for participants' arithmetic task performance $F(2,22)=0.42$, $MSe=53.59$, $p=0.959$.

Figure 4:
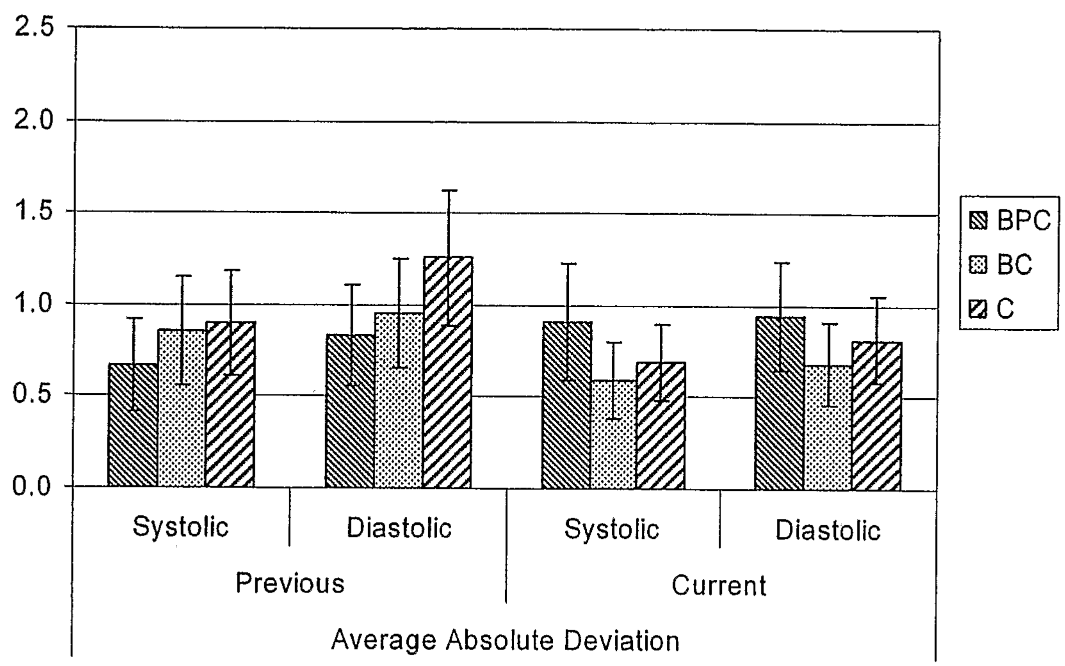
FIG. 4 comprises deviation plots showing the advantage of the beacon in determining the systolic and diastolic values.

The deviation results of FIG. 4 show participants were very accurate at the blood pressure plotting task with all three earcons C, BC and BPC. These results were comparable with Watson, Sanderson and Russell's findings [5] for anaesthetists and were better than the results observed for novices monitoring heart-rate and oxygen saturation with either the pulse oximeter or visual display. These results satisfy the performance criteria of H1 (namely, the accuracy when participants rely on the auditory display alone should be comparable to people's ability to monitor physiological parameters with other auditory displays or visual displays) and H2 (namely, the earcons should be perceivable against background sounds that could be found in the monitoring environment).

Four analyses were conducted of participants' judgment of the earcons, including the main effect of earcon type and the linear contrasts specified in Table 2.

In comparisons L3 and L4, the presence of the beacon significantly improved participants' judgments for the earcon. These results support H3 (namely, the presence of a beacon should assist participants with the interpretation of earcons for systolic and diastolic blood pressure). However, they do not establish whether this was due to an attentional shift by the participants, or because the beacons assisted participants with their judgments of the earcon due to the recognition of the rhythm, pitch and duration. The results of L2 indicated counter H4 (namely, the benefit of historical systolic and diastolic information in the earcon for recalling previous measurements and identifying changes between the previous and current measurements); however, the subjective results indicated that this was due to insufficient exposure to the earcons.

Eight subjective questionnaire responses about the effects of the earcon on participants' perceived workload, memory requirements and task performance were analysed using ANOVAs. Only Question 5: "How much effort was required to remember the previous blood pressure values?" found significant differences between the earcons $F(1,23)=10.97$, $MSe=49.80$, $p=0.000$. A within-subject analysis of the results was significant. The BPC condition was significantly easier to remember than the C and BC condition, Mean difference=−1.623, $MSe=0.461$, $p=0.02$. The BPC condition was significantly easier to remember than the BC condition, Mean difference=−1.246, $MSe=0.341$, $p=0.01$. However the BC condition was not significantly easier to remember than the C condition, Mean difference=−0.377, $MSe=0.257$, $p=0.157$. So although there were no significant participant judgment benefits of the BPC condition, the participants' believed the historical information contained within the BPC to be useful.

The availability of the historical information is likely to be beneficial when participants have had greater exposure to the earcons, as has been the case for extended exposure to Morse code [11]. The historical information is also likely to be of benefit in cases where the time elapsed between blood pressure measurements is longer than two minutes. The subjective results and the conclusions drawn from research into Morse code indicates that H4 (i.e. the benefit of historical systolic and diastolic information in the earcon for recalling previous measurements and identifying changes between the previous and current measurements) is likely to be achieved with more practice and greater elapsed time between earcons.

EXAMPLE 2

Comparison of Earcon Constructs for Intermittent Information

The second experiment addressed issues related to H1, H2, H4 and H5. From a comparison between three of the possible earcons, it was sought to establish that historical information and an auditory alert would assist participants' awareness of the simulated patient's blood pressure. The auditory alert occurred at the same time interval before the systolic information of the earcons as did the beacon in the first experiment; however, the alert was significantly different in pitch, duration and rhythm so it could not be used as a beacon. If the beacon served only to alert participants to reorient their attention from the arithmetic task to the earcon then similar results to the first experiment should have been observed.

The second experiment was a within-subject experiment conducted with three independent variables. The first variable was earcon type. The first earcon provided information about the current systolic and diastolic blood pressure measurements (referred to as C); a second earcon contained the alert followed by the current systolic and diastolic blood pressure measurements (referred to as AC); a third earcon contained the alert followed by the previous historical blood pressure measurements, then the current systolic and diastolic blood pressure measurements (referred to as APC).

Twenty-four new participants, with no medical qualification, underwent training and evaluations of the three conditions. The second experiment only differed from the first in the training and scenario evaluations by the replacement of the beacons with the alerts.

Figure 5:
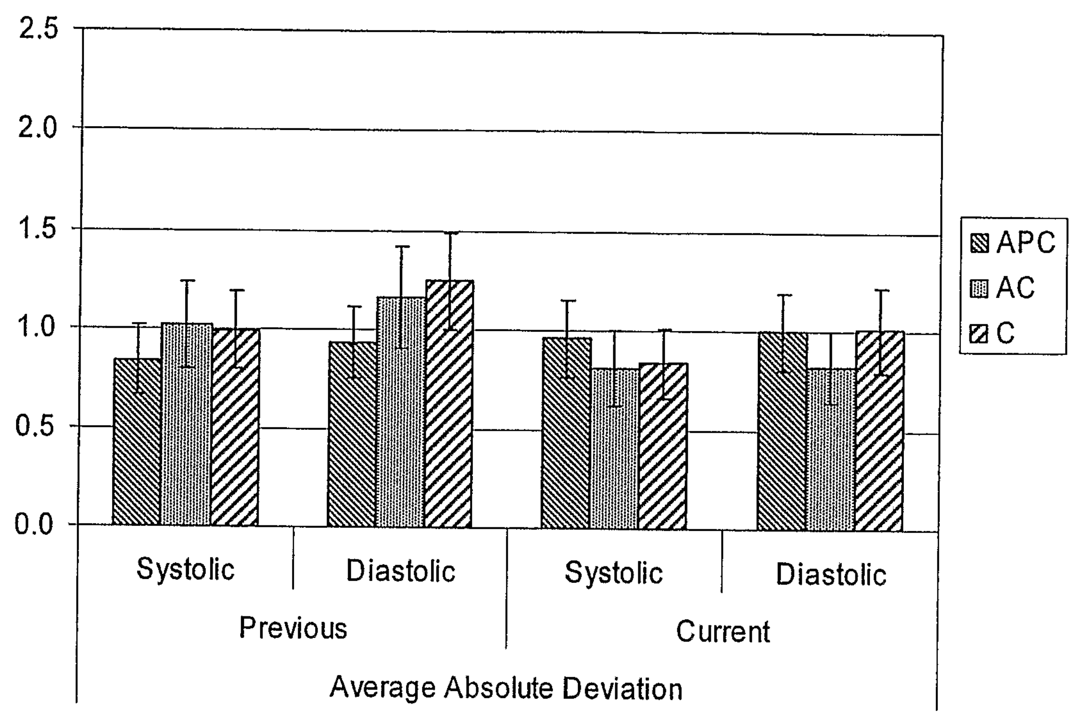
FIG. 5 comprises deviation plots showing the advantage of including historical information in the earcon.

The deviation results in FIG. 5 show participants were very accurate at the blood pressure plotting task with all three earcons C, AC and APC. As with the first experiment, these results support H1 (i.e. the accuracy when participants rely on the auditory display alone should be comparable to people's ability to monitor physiological parameters with other auditory displays or visual displays).

Four analyses were conducted for participants' judgment of the earcons, including the main effect of earcon type and the linear contrasts specified in Table 3.

In comparisons L3 and L4, the presence of the alert did not significantly improve participants' judgments for the earcon. The results of L1 and L2 indicated that there was a trade-off of better participant judgment on the previous measures of systolic and diastolic for slightly inferior performance on the current values. These results indicate that H4 (i.e. the use of historical systolic and diastolic information in the earcon for recalling previous measurements and identifying changes between the previous and current measurements) had the potential to be beneficial with further exposure to the earcons.

The results of the two studies, in conjunction with prior auditory experiments, show that the use of earcons for indicating blood pressure has the ability to accurately convey patient systolic and diastolic blood pressure information. The use of both duration and pitch in a rhythmic pattern allowed participants with no medical training to accurately monitor the patient as well as anaesthetists can monitor the pulse oximeter when the results of Watson and Gill are compared with the finding of Watson, Sanderson and Russell [5],[9]. The beacon significantly improved participants' performance, whilst the historical information showed a trend to better performance, which is likely to be more evident when the intermittent measurements are less frequent. These results only required the participants to remember blood pressure readings whilst clinical staff must monitor several more low level physiological parameters. An increase in the memory load and the possibility that intervals as long as five minutes may elapse between non-invasive blood pressure readings suggest that it is likely that historical information may assist in some circumstances.

The method and apparatus of this invention can assist clinicians to maintain high levels of awareness of patient state and to make better use of blood pressure information in interpreting patient events.

The foregoing describes only one embodiment of the invention and modifications which are obvious to those skilled in the art may be made thereto without departing from the scope of the invention. For example, the invention can be utilised for the sonification of other physiological parameters.

Throughout this specification, including the claims, where the context permits, the term 'comprising' or comprises' is intended to be used in the inclusive sense, i.e. as including the stated integers without necessarily excluding others.

TABLE 1

| | Examples | Likely use |
|---|---|---|
| 1. | $S_c D_c$ | Invasive measures of blood pressure where rapid blood pressure changes are likely to occur |
| 2. | $B_s S_c D_c$ | Invasive measures of blood pressure where the listener(s) may be unfamiliar with the earcon nine-point scale or rate of blood pressure changes are likely to slow |
| 3. | $B_s B_s S_c D_c$ | Non-invasive measures of blood pressure taken at 2 minutes or less time intervals |
| 4. | $B_s B_s S_p D_p S_c D_c$ | Non-invasive measures of blood pressure taken at more than 2 minute time intervals |
| 5. | $B_s B_s S_p D_p B_s B_s S_c D_c$ | Non-invasive measures of blood pressure taken at more than 2 minute time intervals where the listener(s) may be unfamiliar with the earcon nine-point scale |
| 6. | $B_d B_d S_c D_c$ | Non-invasive measures of blood pressure used to detect a change in a patient's state that is exhibiting an abnormal but steady systolic and/or diastolic blood pressure |
| 7. | $B_s M_p M_c$ | Non-invasive measures of blood pressure measurements for long term trend reviewing of the patient's blood pressure history |

| Symbol | Indicates | Description |
|---|---|---|
| B | Beacon | A known comparative sound used by listeners to assist with the identification of other values in the earcon |
| S | Systolic blood pressure | First blood pressure measurement registered during cuff deflation |
| D | Diastolic blood pressure | Second blood pressure measurement registered during cuff deflation |
| M | Mean blood pressure | Average of the systolic and diastolic blood pressure |
| $(*_s)$ | Static beacon | A sound that defines the normal range for systolic and diastolic blood pressure |

TABLE 1-continued

| | | |
|---|---|---|
| $(*_d)$ | Dynamic beacon | A sound that defines the range for systolic and diastolic blood pressure selected by the operator |
| $(*_c)$ | Current measurement | ($n^{th}$) blood pressure measurement |
| $(*_p)$ | Previous measurement | ($n^{th}$ − 1) blood pressure measurement |

TABLE 2

Table 2: The effect of historical information and beacons on participants' judgments for systolic and diastolic blood pressure.

| | Transformed Variable | Sum of Squares | df | Mean Square | F | Sig. |
|---|---|---|---|---|---|---|
| L1 | BC vs. BPC at prior | 2.282 | 1 | 2.282 | 2.779 | .109 |
| L2 | BC vs. BPC at current | 8.027 | 1 | 8.027 | 40.036 | .000 |
| L3 | C vs. BC at prior | 2.947 | 1 | 2.947 | 5.294 | .031 |
| L4 | C vs. BC at current | 1.373 | 1 | 1.373 | 4.431 | .046 |

Scores are the mean error away from the correct score on the nine-point rating scale.

TABLE 3

Table 3: The effect of historical information and alerts on participants' judgments for systolic and diastolic blood pressure.

| | Transformed Variable | Sum of Squares | df | Mean Square | F | Sig. |
|---|---|---|---|---|---|---|
| L1 | AC vs. APC at prior | 4.076 | 1 | 4.076 | 8.865 | 0.007 |
| L2 | AC vs. APC at current | 2.581 | 1 | 2.581 | 7.258 | 0.013 |
| L3 | C vs. AC at prior | 0.094 | 1 | 0.094 | 0.177 | 0.678 |
| L4 | C vs. AC at current | 1.109 | 1 | 1.109 | 2.565 | 0.123 |

Scores are the mean error away from the correct score on the nine-point rating scale.

REFERENCES

1. Miller, R. (1994). Anesthesia, 4th ed. Churchill Livingstone Inc.
2. Sharp, T. D, Helmicki, A. J., "Application of the Ecological Interface Design Approach to Neonatal Intensive Care", Human Factors and Ergonomics Society, 42nd Annual Meeting, October, 1998.
3. Jungk A, Thull B, Hoeft A, Rau G. (2000). Evaluation of two new ecological interface approaches for the anesthesia workplace. J Clin Monitor Comput. 16(4):243-258. Refs: 45/Code: ANE; HMI
4. Zhang Y, Drews F, Westenskow D, Foresti S, Agutter J, Bermudez J, Blike G, Loeb R. (2002). Effects of integrated graphical displays in situation awareness in anesthesiology. Cognition, Technology, and Work. Berlin: Springer.
5. Watson, M., Sanderson, P., & Russell, W. J. (2004). Tailoring reveals information requirements: The case of anaesthesia alarms. Interacting with Computers. 16, 271-293.
6. Seagull, J. F., & Sanderson, P. M. (2001). Anesthesia alarms in context: An observational study. Human Factors, 43, 66-78.
7. Xiao, Y., Mackenzie, C. F., Seagull, F. J., & Jaberi, M. (2000). Managing the monitors: An analysis of alarm silencing activities during an anesthetic procedure. Proceedings of the Joint Meeting of The Human Factors And Ergonomics Society and the International Ergonomics Association (IEA 2000/HFES 2000). (pp. 250-253). Santa Monica, Calif.: HFES.
8. Loeb, R. G., & Fitch, W. T. (2002). A Laboratory Evaluation of an Auditory Display Designed to Enhance Intraoperative Monitoring. Anesthesia & Analgesia, 94:362-368.
9. Watson, M. & Gill, T. (in press) Earcon for Intermittent Information in Monitoring Environments. To appear in the Proceedings of the Australian/New Zealand conference on Computer-Human Interaction (OzCHI04), The University of Wollongong, Australia. 22-24 Nov. 2004
10. Anderson, J., & Sanderson, P. (2004). Designing sonifications for effective attentional control in complex work domains. Proceedings of the 48th Annual Meeting of the Human Factors and Ergonomics Society. HFES: Santa Monica, Calif.
11. Bryan, W. L., & Harter, N. (1897). Studies in the physiology and psychology of telegraphic language. Psychological Review, 4, 27-53.

The invention claimed is:

1. A method of representing or displaying blood pressure of a subject aurally, comprising the steps of receiving an electronic signal representative of a blood pressure measurement, and synthesising a non-vocal audio output from the signal using an electronic signal processor, wherein the audio output is an earcon and both a duration and a pitch of the earcon are dependent on the blood pressure measurement, wherein the pitch of the earcon is dependent on the blood pressure measurement according to a stepped scale, and wherein the duration of the earcon is dependent on the blood pressure measurement according to a stepped scale, and wherein the blood pressure measurement is one of arterial systolic, diastolic and mean blood pressure, or one of pulmonary arterial systolic, diastolic and mean blood pressure measurements, and the earcon comprises a tone or sequence of tones.

2. A method as claimed in claim 1, further comprising the step of outputting the audio output through a speaker or earpiece.

3. A method as claimed in claim 1, wherein the earcon further includes an initial tone representing a previous blood pressure measurement.

4. A method as claimed in claim 1, wherein the earcon further includes a beacon tone representing a predetermined value of a blood pressure parameter.

5. A method as claimed in claim 1, further comprising the step of generating an auditory prompt signal prior to each earcon.

6. A method as claimed in claim 1, wherein the earcon includes a plurality of tones, further comprising the step of aurally distinguishing the tones by adding harmonics to the primary frequencies of the tones.

7. A method as claimed in claim 1, wherein the stepped scale associated with the duration is a three part scale.

8. A method as claimed in claim 1, wherein the stepped scale associated with the pitch is a three part scale.

9. An apparatus for representing or displaying blood pressure of a subject aurally, comprising an audio synthesizer adapted to receive a signal representative of blood pressure measurement and to synthesize an audio output from the signal, wherein the audio synthesizer operatively produces a non-vocal audio output in the form of an earcon and both a duration and a pitch of the earcon are dependent on the value of the blood pressure measurement, wherein the pitch of the earcon is dependent on the blood pressure measurement according to a stepped scale, and wherein the duration of the earcon is dependent on the blood pressure measurement according to a stepped scale, and wherein the blood pressure measurement is one of arterial systolic, diastolic and mean blood pressure, or one of pulmonary arterial systolic, diastolic and mean blood pressure measurements, and the earcon comprises a tone or sequence of tones.

10. Apparatus as claimed in claim 9, further comprising a user interface for varying characteristics of the earcon.

11. Apparatus as claimed in claim 9, further comprising a signal processor for receiving the blood pressure measurement and deriving the signal therefrom, the signal processor having an output connected to the audio synthesizer.

12. Apparatus as claimed in claim 9, further comprising a memory for storing at least one previous blood pressure measurement, and wherein the earcon further includes an initial tone representing a previous blood pressure measurement.

* * * * *